(12) United States Patent
Barnett (10) Patent No.: US 10,070,812 B2
(45) Date of Patent: Sep. 11, 2018

(54) METHOD FOR IMPROVED SEIZURE DETECTION

(71) Applicant: SBB Research Group LLC, Northbrook, IL (US)

(72) Inventor: Samuel Benjamin Barnett, Northbrook, IL (US)

(73) Assignee: SBB Research Group LLC, Northbrook, IL (US)

( * ) Notice: Subject to any disclaimer, the term of this patent is extended or adjusted under 35 U.S.C. 154(b) by 0 days.

(21) Appl. No.: 15/449,023

(22) Filed: Mar. 3, 2017

(65) Prior Publication Data

US 2017/0251969 A1    Sep. 7, 2017

Related U.S. Application Data (60) Provisional application No. 62/302,896, filed on Mar. 3, 2016.

(51) Int. Cl.
| | | |
|---|---|---|
| *A61B 5/0476* | (2006.01) | |
| *A61B 5/04* | (2006.01) | |
| *A61B 5/00* | (2006.01) | |

(52) U.S. Cl.
CPC ........ *A61B 5/4094* (2013.01); *A61B 5/04017* (2013.01); *A61B 5/0476* (2013.01); *A61B 5/7257* (2013.01)

(58) Field of Classification Search
CPC . A61B 5/4094; A61B 5/04017; A61B 5/0476; A61B 5/7257
USPC ................................................ 600/544, 545
See application file for complete search history.

(56) References Cited

U.S. PATENT DOCUMENTS

| | | | |
|---|---|---|---|
| 6,366,813 B1 * | 4/2002 | DiLorenzo | A61B 5/048 607/45 |
| 6,473,644 B1 * | 10/2002 | Terry, Jr. | A61N 1/3627 607/2 |
| 6,477,399 B2 | 11/2002 | Biswal et al. | |
| 6,622,041 B2 * | 9/2003 | Terry, Jr. | A61N 1/36114 607/2 |
| 8,296,172 B2 | 10/2012 | Marci et al. | |
| 8,335,715 B2 | 12/2012 | Pradeep et al. | |
| 8,382,667 B2 * | 2/2013 | Osorio | A61N 1/36139 600/301 |
| 8,462,996 B2 | 6/2013 | Moon et al. | |
| 8,494,905 B2 | 7/2013 | Pradeep et al. | |
| 8,615,309 B2 * | 12/2013 | Craig | A61N 1/36082 607/118 |
| 8,635,105 B2 | 1/2014 | Pradeep et al. | |
| 9,056,195 B2 * | 6/2015 | Sabesan | A61N 1/36139 |
| 9,179,858 B2 | 11/2015 | Hasson et al. | |
| 9,302,109 B2 * | 4/2016 | Sabesan | A61B 5/0205 |
| 2007/0233193 A1 * | 10/2007 | Craig | A61N 1/36082 607/2 |

(Continued)

*Primary Examiner* — Navin Natnithithadha
(74) *Attorney, Agent, or Firm* — Jeffrey Schox; Thomas Gwinn (57) ABSTRACT

A method for improved seizure detection includes capturing neural data for a first set of brain regions; calculating inter-region correlations between pairs of the first set of brain regions from the neural data; detecting a period of hyposynchrony from the inter-region correlations; after detecting the period of hyposynchrony, detecting a period of hypersynchrony from the inter-region correlations; and based on a transition from the period of hyposynchrony to the period of hypersynchrony, detecting a first seizure.

19 Claims, 3 Drawing Sheets

(56) References Cited

U.S. PATENT DOCUMENTS

| | | |
|---|---|---|
| 2010/0094702 A1 | 4/2010 | Silberstein |
| 2014/0277255 A1* | 9/2014 | Sabesan ............. A61N 1/36139 607/45 |
| 2015/0005839 A1* | 1/2015 | Sabesan ............. A61N 1/36064 607/45 |
| 2015/0238761 A1* | 8/2015 | Sabesan ............. A61N 1/36139 607/45 |
| 2015/0306392 A1* | 10/2015 | Sabesan ............... A61B 5/0205 607/45 |

* cited by examiner

METHOD FOR IMPROVED SEIZURE DETECTION

CROSS-REFERENCE TO RELATED APPLICATIONS

This application claims the benefit of U.S. Provisional Application Ser. No. 62/302,896, filed on 3 Mar. 2016, which is incorporated in its entirety by this reference.

TECHNICAL FIELD

This invention relates generally to the neurology field, and more specifically to new and useful new and useful methods for improved seizure detection.

BACKGROUND

Epilepsy is a group of diseases, characterized by recurrent seizures, that affect over 65 million people worldwide. In many people with epilepsy, seizures can occur at any time, often without discernable warning. This is extremely disruptive to the lives of epilepsy sufferers; and may prevent them from engaging in activities in which their lives (or the lives of others) may be endangered by the unexpected onset of a seizure. These activities may include driving, operating heavy machinery, and many outdoor activities.

The ability to predict seizures (even only a few seconds in advance) could greatly reduce the detriment of epilepsy; but unfortunately, there are no known effective methods of seizure prediction. More generally, the mechanisms behind why seizures start (and stop) are poorly understood.

Thus, there is a need in the field of neurology to create a method for improved seizure detection. This invention provides such new and useful methods.

DESCRIPTION OF THE INVENTION EMBODIMENTS

The following description of the invention embodiments of the invention is not intended to limit the invention to these invention embodiments, but rather to enable any person skilled in the art to make and use this invention.

1. Method for Improved Seizure Detection

Figure 1:
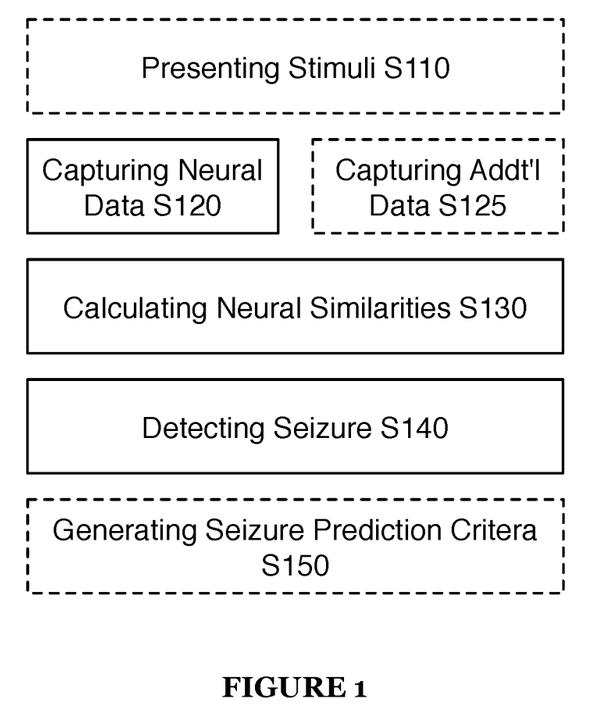
FIG. 1 is a chart view of a method of a preferred embodiment.
Figure 2:
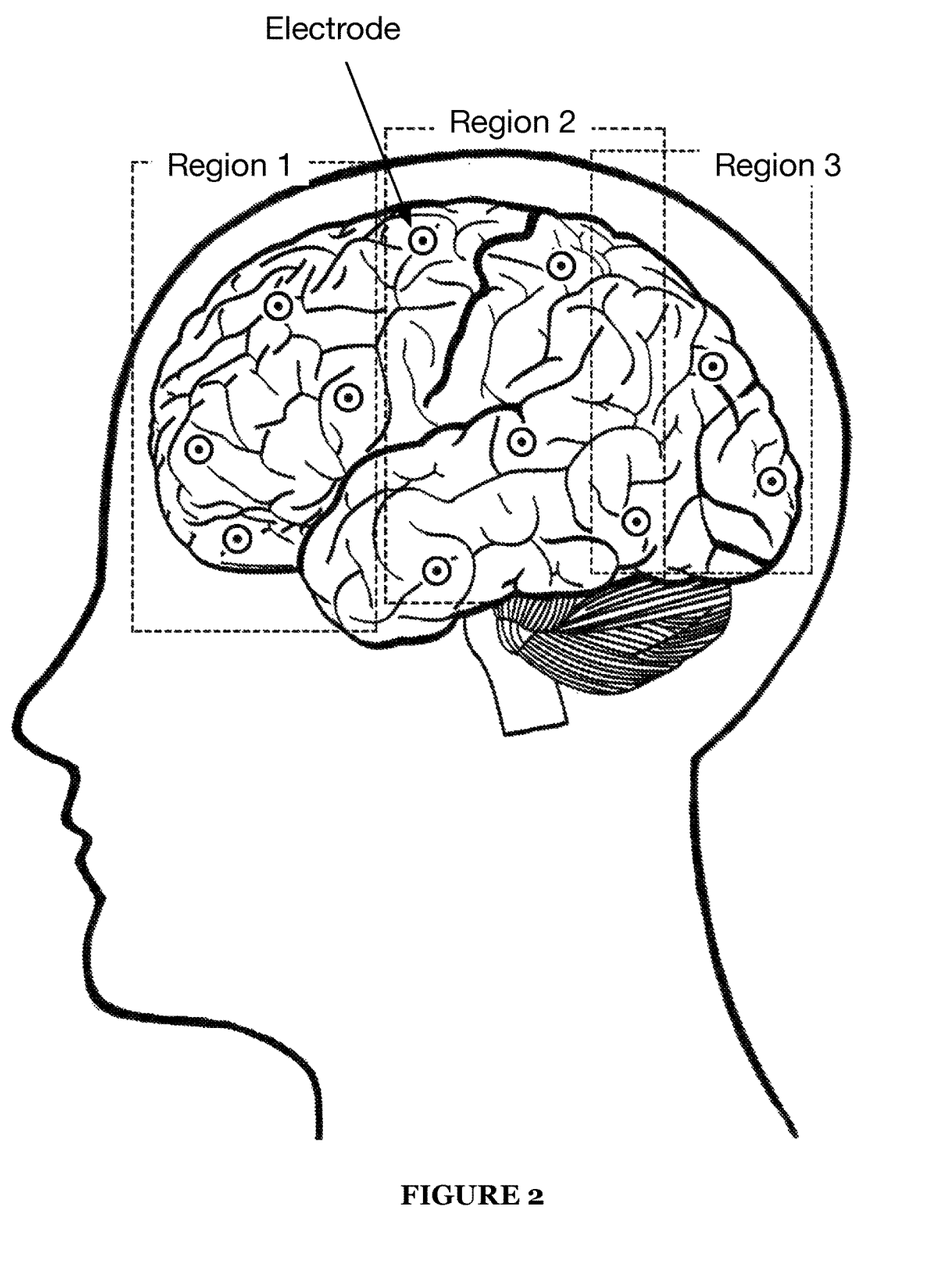
FIG. 2 is diagram view of capturing neural data of a method of a preferred embodiment.

As shown in FIG. 1, a method 100 for improved seizure detection includes capturing neural data for a set of brain regions S120, calculating neural similarities for the set of brain regions S130, and detecting a seizure using the neural similarities S140. The method 100 may additionally or alternatively include capturing additional data S125 and/or generating seizure prediction criteria S150.

The method 100 functions to detect seizures based on neural similarity data between regions of the brain; neural data is captured in S120, similarities are calculated in S130, and the similarities are analyzed for seizure detection in S140. Seizure detection may be paired with the presentation of particular stimuli (in S110) and/or further analysis of neural data (captured in S120) or additional data (captured in S125) to generate seizure prediction criteria (S150).

The method 100 preferably implements a novel seizure detection algorithm based on a two-step process: detecting a period of brain region hyposynchrony (decreased synchronization between brain regions) followed by a period of brain region hypersynchrony (increased synchronization between brain regions). While the role of hypersynchrony as characteristic of seizures is well-known, the role of hyposynchrony is debated. Accordingly, while synchrony has been used to detect seizures in the past, the focus on the transition from hypo- to hypersynchrony is a trailblazing aspect of the method 100; having the potential to predict seizures earlier and with more accuracy than traditional methods.

Further, the method 100 preferably detects hyposynchrony and hypersynchrony based on pairwise correlations between brain regions, instead of traditionally used overall brain synchrony (or average synchrony in a particular brain region).

Finally, the method 100 may include referencing the pairwise correlations to a library of historical correlation levels to better detect the presence of hyposynchrony and hypersynchrony.

Presenting stimuli S110 functions to present stimuli which may affect the presence, magnitude, and/or other characteristics of seizures. Additionally or alternatively, presenting stimuli S110 may function to enhance the correlation between captured neural data and compared historical data (serving as a reference stimuli). Stimuli may deal with any sensory modality or combination of sensory modalities (e.g., taste, touch, smell, direct brain stimulation). For example, stimuli may comprise audiovisual stimuli, electrical impulse stimuli, application of heat/cold, etc. As another example, stimuli may comprise a patient executing physical or mental activity.

In some cases, stimuli may comprise or be related to potential seizure triggers. For example, S110 may include raising a patient's blood alcohol content (BAC) (e.g., by having the patient drink alcohol). S110 may additionally or alternatively include altering a patient's medication regimen (or any other behavior of a patient). This may, for example, allow seizure data to be collected that will provide a better baseline for future seizures for a given patient or for a class of patients (e.g. patients of a particular demographic, patients who drink, patients experiencing a particular type of seizure, etc.). A potential seizure trigger may be any stimuli known or suspected to cause seizures in a patient or class of patients.

Stimuli presented in S110 are preferably synchronized to neural data captured in S120. This may include, for example, correcting for a latency between application of a stimulus and effect on a subject's brain. Obviously, synchronization may be different for different stimuli. Additionally or alternatively, stimuli may be unsynchronized to neural data capture.

Stimuli may be synchronized in any manner; for example, neural data or other data (e.g., heart rate, perspiration, heart rate, user responses, BAC, etc.) may be used to detect patient response to a stimulus over time; the stimuli may then be synchronized based on the comparison between patient response data and the neural data used to detect seizures. For example, a flashing light may be displayed to a patient. Neural data of the patient may then be monitored to detect neural response to the flashing light (which is delayed from the flash itself). The stimulus may be synchronized thusly to seizure neural data by adjusting for this delay.

Capturing neural data for a set of brain regions S120 functions to capture neural data from subjects prior to, during, and after onset of a seizure. S120 preferably includes capturing neural data for multiple brain regions, such that neural data from those regions may be compared in S130.

As the onset of seizure is preferably detected using captured neural data, the neural data is preferably inherently linked temporally to seizure detection; however, seizure detection may additionally or alternatively be performed in another manner (e.g., by observing a patient), in this case, captured neural data is preferably synchronized temporally to seizure detection. For example, in some cases, captured neural data may not be sufficiently accurate to identify seizures alone (e.g., prior to calibrating hypo- and/or hyper-synchrony thresholds)

Capturing neural data S120 preferably includes capturing electroencephalography (EEG) data, but may additionally or alternatively include capturing functional Magnetic Resonance Imaging (fMRI) data, electrocorticography (ECoG) data, functional near-infrared spectroscopy (fNIRS) data, Magnetoencephalography (MEG), and/or any other suitable neural data.

Step S120 preferably includes capturing EEG data by placing electrodes on the scalp of a subject and measuring electrical activity in-brain as recorded by the electrodes. Step S120 preferably includes collecting EEG data via a low-density electrode array (e.g., thirty-two or fewer electrodes), but may additionally or alternatively include collecting EEG data using electrode arrays of any density. Electrode arrays may be spatially fixed (e.g., electrodes are attached to a cap worn by a subject; the distance between electrodes is fixed), but may alternatively be free (e.g., electrodes are placed manually on a person's scalp and can be positioned in any pattern). EEG data may be represented using any montage (e.g., sequential montage, referential montage, average reference montage, laplacian montage, actiCAP 64Ch Standard-2 montage). In this variation, Step S120 preferably includes capturing data from electrodes individually, but may additionally or alternatively include averaging data from several electrodes. For example, the data from three electrodes may be averaged together.

EEG data collected preferably includes neural activity as the power (dB) of alpha oscillations (also known as Berger's wave) but may additionally or alternatively include any measurement of neural activity (e.g., signal strength, phase, periodicity, frequency, etc.).

In a variation of a preferred embodiment, S120 include capturing fMRI data. Capturing fMRI data preferably includes capturing blood-oxygen-level dependent (BOLD) contrast signals, but may additionally or alternatively include capturing temperature contrast signals, pH contrast signals, calcium-sensitive agent contrast signals, neuronal magnetic field contrast signals, Lorentz-effect signals, and/or any other suitable type of signals. fMRI data is preferably captured over a three-dimensional volume by scanning a series of two-dimensional slices.

Capturing neural data S120 may additionally include capturing anatomical neural data. Capturing anatomical neural data preferably includes capturing anatomical neural data using a magnetization-prepared rapid-acquisition gradient echo (MPRAGE) pulse sequence, but alternatively may include capturing anatomical neural data by any other suitable method.

In a second variation of a preferred embodiment, Step S120 includes capturing EEG data and FRMI data simultaneously (e.g., by using an FMRI compatible EEG array). Step S120 may include any combination of multiple types of capturing neural data.

Capturing neural data S120 preferably also includes processing the raw data. Processing the raw data preferably includes transforming raw data to prepare it for visualization or later calculations. Processing the raw data preferably also includes aligning the data to reference markers and filtering the data to remove noise and artifacts.

EEG data is preferably filtered (e.g., by high-pass filtering at 1 Hz and low-pass filtering at 70 Hz) to remove high and low frequency artifacts. EEG data may additionally or alternatively be filtered or processed in any suitable manner (e.g., passed through a 60 Hz notch filter to remove powerline noise). For example, EEG data may be processed to remove eye-induced artifacts (e.g., eye blinks), cardiac artifacts, and/or muscle activation artifacts. Independent component analysis techniques may be used to process EEG data.

In one example embodiment, EEG data is filtered by performing a Short-Time Fourier Transform (STFT) of the raw EEG data at each timestep, filtering the resulting Power Spectral Density (PSD) matrix, and multiplying the common logarithm (base 10) of the PSD matrix by 10; then assembling a time series of activity at the given electrode site.

EEG frequency windows (as set by high/low pass filters), sampling rates, and/or any other EEG measurement parameters (or environmental parameters) may be adjusted to optimize or otherwise modify results of seizure detection in S140.

fMRI data is preferably 3D motion corrected and slice scan time corrected, followed by a linear trend removal and high pass filtering. Spatial smoothing is preferably then applied to the fMRI data. The fMRI data is preferably transformed to 3D Talairach spaces and projected upon reconstructions of cortical surfaces generated from captured anatomical neural data. The fMRI data may alternatively be processed in any other way (or not processed at all). For example, the fMRI data may be transformed and/or reregistered according to the MNI atlas from the Montreal Neurological Institute instead of according to the Talairach atlas. BOLD contrast signals are preferably processed as well; the mean white matter signal is preferably projected out from the BOLD signal in each voxel of fMRI data in each subject. For each subject, the mean BOLD signal is preferably calculated and entered into a linear regression to predict the BOLD signal in each voxel; the BOLD signals are preferably then replaced with the residuals resulting from this regression.

If fMRI and EEG data is captured simultaneously, the data may be processed to remove artifacts introduced by using both neural data capture methods simultaneously (e.g., MRI gradient artifacts may be removed from fMRI data, while ballistocardiographic artifacts may be removed from EEG data). EEG and fMRI data may also be temporally re-synchronized (since data derived from fMRI may occur over a different time course than data derived from EEG).

Processing the raw data may additionally or alternatively include processing data based on additional data captured by S125. For example, if it is known that degrees of hyposynchrony prior to seizure onset are dependent on air temperature of a room, neural data from subjects may be transformed on the basis of temperature. As another example, eye tracking data may be used to remove artifacts associated with eye movement from EEG data.

Capturing neural data S120 may additionally or alternatively include checking captured neural data for neural abnormalities. For example, after neural data is captured, it may be examined (either manually or automatically) to detect abnormalities or issues in the brains of subjects. If abnormalities are detected, the captured neural data in which abnormalities are detected may be flagged to allow for seizure detection mechanisms to be adjusted. Neural abnormalities may include any effects that result in non-neurotypical brain response.

Neural abnormalities may be detected in any manner; for example, by identifying characteristics of captured neural data that are outside of reference ranges or deviate from a reference value by a threshold amount.

Capturing additional data S125 functions to capture data additional to the neural data captured by S120. Additional data may include subject response data, subject descriptive data, environmental data, and/or other data. Subject response data preferably includes data on how subject behavior, biomarkers, or other characteristics of subject response (e.g., to stimuli presented in S110). Subject response data may include measured responses, such as biometric data (e.g., heart rate or perspiration), eye tracking data, and facial recognition data. Additional examples of biometric data include pupil dilation, blood pressure, body temperature, typing rhythm, gait, posture, and speech characteristics. Subject response data may also include reported responses, such as self-reported ratings from subjects or tests of subject mental or physical performance.

Subject descriptive data preferably includes demographic data on the subjects; for example, their age, race and gender. Subject descriptive data may also include more specific data relating to a person, such as a list of their recent purchases or their tastes in movies. Subject descriptive data may be collected manually (e.g., by querying a subject) or automatically as part of the method 100 (e.g., by downloading information about a subject from a social media platform).

Environmental data preferably includes data pertaining to the environment stimuli are presented in; for example, temperature, time of presentation, light level, and level of background noise in the environment. Environmental data may include data captured by sensors including thermometers, light sensors, cameras, microphones, barometers, hygrometers, etc.

Calculating neural similarities for the set of brain regions S130 functions to calculate similarity levels between sets of captured neural data corresponding to various regions of a subject's brain.

Sets of neural data may be processed before calculating neural similarity; for instance, neural data from certain regions of the brain may be scaled or otherwise transformed to account for differences between those regions (or the neural data capture process for those regions) and other regions of the brain.

Calculating neural similarity preferably includes calculating cross-brain correlations on each possible pairing of brain regions. In the case of EEG, each region may correspond to one or more EEG electrodes. If a brain region corresponds to multiple EEG electrodes, brain regions preferably do not overlap (i.e., there is no intersection between a set of electrodes in one region and a set of electrodes in another); alternatively, brain regions may overlap (i.e., there is some intersection between a set of electrodes in one region and a set of electrodes in another).

For example, if there are three regions A, B, and C, inter-region correlations would be calculated for the A, B pair, the A, C pair, and the B, C pair. Calculating neural similarity may additionally or alternatively include calculating inter-region correlations between only a subset of possible pairings, and/or calculating neural similarity using another method. Calculating neural similarity preferably includes calculating neural similarity at each EEG or fMRI timestep (e.g., using a rolling correlation of several previous samples), but alternatively may include calculating neural similarity according to any other suitable timing (e.g., a correlation window that encompasses several neural data collection timesteps). Calculating neural similarity preferably includes calculating neural similarity across entire neural datasets corresponding to each person (i.e. all of the spatial data captured at each time step) but may alternatively include calculating neural similarity over only a spatial and/or temporal subset of neural datasets. For example, a set of neural data may be not used for neural similarity calculations if the corresponding subject moved too much during data collection, or if the collected data is obviously corrupted, or if the subject failed to follow instructions.

Sets of neural data to be removed from neural similarity calculations may be detected by identifying the data sets to be removed as statistical outliers (e.g., data sets with multiple data points more than three standard deviations from mean values), but may additionally or alternatively be detected in any way (e.g., particular markers of abnormal response).

In one example embodiment, inter-region correlations are calculated by computing alpha wave power measurements for a given region and time period (i.e., a set of timesteps) and comparing these alpha wave power measurements with measurements for a different region and for the same time period. Additionally or alternatively, the method 100 may include comparing data from one region and time period to data from the same region and another time period; or comparing data from one region and time period to another region and another time period.

Detecting a seizure using the neural similarities S140 functions to enable seizure onset to be detected by analysis of neural data.

Figure 3:
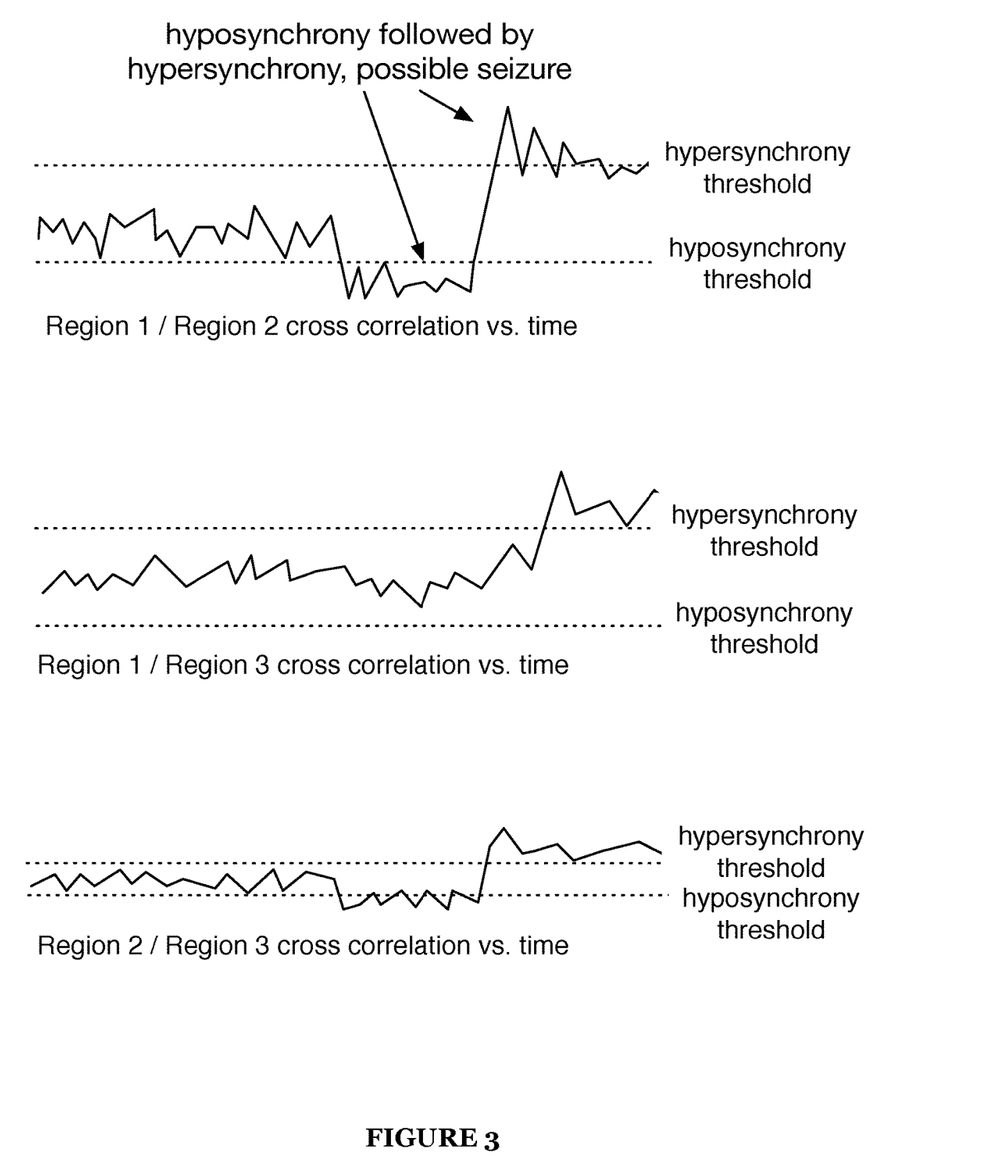
FIG. 3 is an example plot view of seizure detection of a method of a preferred embodiment.

S140 preferably includes detecting a period of hyposynchrony followed by a period of hypersynchrony between one or more pairs of a set of brain region pairs (e.g., via inter-region correlations), as shown in FIG. 3.

S140 preferably includes detecting hyposynchrony for a brain region pair by detecting that an inter-region correlation for that pair has dropped below a hyposynchrony threshold, but may additionally or alternatively include detecting hyposynchrony in any manner. For hyposynchrony to be detected, S140 may additionally include detecting that an inter-region correlation pair has dropped below a hyposynchrony threshold for a threshold period (referred to as a hyposynchrony time threshold).

Likewise, S140 preferably includes detecting hypersynchrony for a brain region pair by detecting that an inter-region correlation for that pair has risen above a hypersynchrony threshold, but may additionally or alternatively include detecting hypersynchrony in any manner. For hypersynchrony to be detected, S140 may additionally include detecting that an inter-region correlation pair has risen above a hypersynchrony threshold for a threshold period (referred to as a hypersynchrony time threshold).

S140 preferably detects a period of hyposynchrony followed by a period of hypersynchrony by detecting that a hypersynchrony threshold trigger occurs within some time period after detecting that a hyposynchrony threshold trigger occurs (referred to as an inter-period time threshold). S140 may additionally or alternatively include detecting that synchrony does not return to typical values (e.g., substantially between thresholds) for a significant period of time between hyposynchrony and hypersynchrony.

S140 preferably includes setting hyposynchrony and hypersynchrony thresholds, including time thresholds, independently for each brain region pair (e.g., each inter-brain correlation data stream). Alternatively, S140 may include setting the same thresholds for each brain region pair, or setting thresholds in any manner.

In a first variation of a preferred embodiment, S140 includes modifying hyposynchrony/hypersynchrony thresholds based on additional data collected in S125 (e.g., subject response data, subject descriptive data, environmental data). In a first example of this variation, S140 includes modifying thresholds based on subject heartrate; the thresholds are set according to an algorithm that takes subject heartrate as an input. In a second example of this variation, S140 includes modifying thresholds based on time of day (e.g., thresholds are different if a subject is being monitored in the morning, rather than the afternoon).

In a second variation of a preferred embodiment, S140 includes modifying hyposynchrony/hypersynchrony thresholds based on historical neural data (e.g., as collected in S120). For example, S140 may include modifying thresholds based on an observation of inter-region correlation variance; if inter-region correlation variance is low over time, this may suggest that changes in inter-region correlation may be significant on a smaller scale, and S140 may include adjusting thresholds accordingly.

S140 may additionally or alternatively harness both additional data and historical neural data to modify hyposynchrony/hypersynchrony thresholds. For example, S140 may include receiving subject demographic data and modifying hyposynchrony thresholds based on historical neural data (or models/characteristics of historical neural data) corresponding to other subjects having similar subject demographic data. For example, the thresholds for a white male in his twenties may be set differently than for an Asian female in her forties, according to historical neural data corresponding to persons of those demographics.

S140 preferably includes detecting a seizure by identifying a period of hyposynchrony followed by a period of hypersynchrony for a single brain region pair, but may additionally or alternatively include detecting a seizure by identifying such events for multiple region pairs (e.g., seizure detection may not occur unless three of six pairings exhibit the hyposynchrony to hypersynchrony pattern).

S140 may include detecting a seizure based on any characteristics of the transition from hyposynchrony to hypersynchrony. In a first example, for seizure detection to be triggered, the transition from hyposynchrony to hypersynchrony (e.g., from below the hyposynchrony threshold to above the hypersynchrony threshold) must occur within a time period less than some transition time threshold. In a second example, for seizure detection to be triggered, hypersynchrony must last longer than a threshold time, where the threshold time is set by the detected period of hyposynchrony (e.g., if a hyposynchrony lasts for 20 ms, hypersynchrony must last for $f(20\ ms)$ where $f$ is a function that produces the hypersynchrony minimum duration based on the hyposynchrony duration).

As with neural similarities in general, the algorithm for seizure detection may vary based on a number of factors; e.g., the duration of hyposynchrony, the magnitude of hyposynchrony, the duration of hypersynchrony, the magnitude of hypersynchrony, modulation of synchrony (e.g., how the synchrony magnitude changes over time), the specific brain region pairs being examined, the size or relative size of brain region pairs being examined, historical data, and/or environmental data.

S140 may additionally or alternatively include detecting seizures in any manner; for example, by detecting only hyposynchrony exceeding a threshold time period.

In one example embodiment, S140 includes training seizure detection methods (e.g., adjusting thresholds) based on other seizure detection methods (e.g., clinical observation, fMRI, etc.).

S140 preferably includes detecting seizure onset, but may additionally or alternatively include detecting seizure duration, severity, seizure focus, or any other characteristics of seizure. Seizure focus may be found using by comparing inter-region correlations for several region pairs and referencing said information to knowledge of how the electrodes for each region corresponds to actual or functional brain structure.

S140 may additionally include tagging (or otherwise identifying) neural data captured in S120 with seizure detection events (or characteristics) to enable analysis of said data to improve future seizure detection. For example, S140 may include identifying certain brain region pairs as more predictive of seizures (generally, for specific types of seizures, for specific patients, and/or for specific classes of patients).

Generating seizure prediction criteria S150 functions to identify characteristics that might be used to predict onset of future seizures (either for a specific patient or for a broader group of patients). S150 preferably includes analyzing neural data captured in S120 and/or additional data captured in S125 in an attempt to discover data patterns preceding a seizure (or data patterns corresponding to some characteristic of a seizure).

For example, a period of hyposynchrony exhibiting certain electrical characteristics (e.g., modulation pattern, phase, magnitude, duration) may be used to predict a seizure. As another example, periods of alternating hyposynchrony and hypersynchrony may be used to predict a seizure. Note that periods of normal synchrony may also factor into seizure detection or prediction. Additionally or alternatively, any patterns of neural data and/or other data may be used to predict seizures.

For example, heart rate data found in S125 may display a predictive ability with regard to seizures for a particular patient. This data could then be used by the patient to provide an early warning (through use of a heart rate monitor) of seizures, allowing them to better prepare for the seizure.

Seizure prediction criteria may also be used to predict seizure characteristics other than onset (e.g., duration, severity, seizure type, cognitive impairment level, physical impairment level, convulsion characteristics). For example, even if seizure onset is not predictable (or does not give enough time for reaction), seizure severity may be predictable based on some collected data. For example, accelerometer data as measured by a device worn on a patient's shirt may correspond to seizure severity. Such data may be collected and used to properly respond to seizures (e.g., if seizure severity and/or duration is above some threshold, emergency personnel may be automatically notified by a patient's smartphone).

The methods of the preferred embodiment and variations thereof can be embodied and/or implemented at least in part as a machine configured to receive a computer-readable medium storing computer-readable instructions. The instructions are preferably executed by computer-executable components preferably integrated with a neural data capture system. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

I claim:

1. A method for improved seizure detection comprising:
   capturing neural data for a first set of brain regions;
     wherein capturing neural data comprises:
       capturing EEG data, at a plurality of electrode channels and at a plurality of timesteps, for the first set of brain regions;
       performing a Short-time Fourier Transform upon the EEG data at each timestep of the set of timesteps, for each electrode channel of the plurality of electrode channels, to generate a Power Spectral Density matrix; and
       filtering the Power Spectral Density matrices;
   calculating inter-region correlations between pairs of the first set of brain regions from the neural data;
   detecting a period of hyposynchrony from the inter-region correlations; wherein detecting the period of hyposynchrony comprises detecting that a first pair of the first set of brain regions is associated with an inter-region correlation below a first hyposynchrony threshold;
   after detecting the period of hyposynchrony, detecting a period of hypersynchrony from the inter-region correlations; wherein detecting the period of hypersynchrony comprises detecting that the first pair of the brain regions is associated with an inter-region correlation above a first hypersynchrony threshold
   detecting a first seizure based on a transition from the period of hyposynchrony to the period of hypersynchrony; and
   notifying a patient or medical care provider of detection of the first seizure.

2. The method of claim 1, further comprising averaging the Power Spectral Density matrices across subsets of the plurality of electrode channels.

3. The method of claim 1, wherein detecting the first seizure comprises detecting that the transition satisfies an inter-period time threshold.

4. The method of claim 3, wherein detecting the first seizure further comprises detecting that the period of hyposynchrony satisfies a hyposynchrony time threshold and that the period of hypersynchrony satisfies a hypersynchrony time threshold.

5. The method of claim 1, wherein detecting the period of hyposynchrony further comprises detecting that a second pair of the first set of brain regions is associated with an inter-region correlation below a second hyposynchrony threshold; wherein detecting the period of hypersynchrony further comprises detecting that the second pair of the first set of brain regions is associated with an inter-region correlation above a second hypersynchrony threshold.

6. The method of claim 5, wherein the first and second hyposynchrony thresholds are non-identical; wherein the first and second hypersynchrony thresholds are non-identical.

7. The method of claim 6, wherein detecting the first seizure comprises detecting that the transition satisfies an inter-period time threshold, that the period of hyposynchrony satisfies a hyposynchrony time threshold, and that the period of hypersynchrony satisfies a hypersynchrony time threshold.

8. The method of claim 1, further comprising capturing a first set of environmental data during the first seizure and generating a correlation of the transition to the first set of environmental data.

9. The method of claim 8, further comprising using the correlation to modify the first hyposynchrony threshold or the first hypersynchrony threshold in response to changes in captured environmental data.

10. The method of claim 8, further comprising using the correlation to predict a second seizure in response to changes in captured environmental data.

11. The method of claim 1, further comprising capturing a first set of subject response data during the first seizure and generating a correlation of the transition to the first set of subject response data.

12. The method of claim 11, further comprising using the correlation to modify the first hyposynchrony threshold or the first hypersynchrony threshold in response to changes in captured subject response data.

13. The method of claim 11, further comprising using the correlation to predict occurrence of a second seizure in response to changes in captured subject response data.

14. The method of claim 1, further comprising, after the first seizure, modifying the first hyposynchrony threshold or the first hypersynchrony threshold based on neural data captured prior to and during the first seizure.

15. A method for improved seizure detection comprising:
   capturing neural data for a first set of brain regions;
   calculating inter-region correlations between pairs of the first set of brain regions from the neural data;
   detecting a period of hyposynchrony from the inter-region correlations; wherein detecting the period of hyposynchrony comprises detecting that a first pair of the first set of brain regions is associated with an inter-region correlation below a first hyposynchrony threshold;
   after detecting the period of hyposynchrony, detecting a period of hypersynchrony from the inter-region correlations; wherein detecting the period of hypersynchrony comprises detecting that the first pair of the brain regions is associated with an inter-region correlation above a first hypersynchrony threshold;
   detecting a first seizure based on a transition from the period of hyposynchrony to the period of hypersynchrony;
   notifying a patient or medical care provider of detection of the first seizure;
   after the first seizure, modifying the first hyposynchrony threshold or the first hypersynchrony threshold based on neural data captured prior to and during the first seizure;
   capturing additional neural data for the first set of brain regions;
   calculating inter-region correlations between pairs of the first set of brain regions from the additional neural data;
   detecting a second period of hyposynchrony from the inter-region correlations; after detecting the second period of hyposynchrony, detecting a second period of hypersynchrony from the inter-region correlations; and detecting a second seizure based on a second transition from the second period of hyposynchrony to the second period of hypersynchrony.

16. The method of claim 15, further comprising capturing a first set of subject response data during the first seizure, generating a correlation of the transition to the first set of subject response data, and using the correlation to predict a severity of the second seizure prior to an end of the second seizure.

17. The method of claim 1, further comprising analyzing the neural data to identify neural abnormalities; further comprising using neural abnormalities to aid in seizure prediction.

18. A method for improved seizure detection comprising:
capturing neural data for a first set of brain regions;
calculating inter-region correlations between a plurality of pairs of the first set of brain regions from the neural data;
detecting a period of hyposynchrony from the inter-region correlations; wherein detecting the period of hyposynchrony comprises detecting that the plurality of pairs of the first set of brain regions are associated with inter-region correlations below a set of hyposynchrony thresholds;
after detecting the period of hyposynchrony, detecting a period of hypersynchrony from the inter-region correlations; wherein detecting the period of hypersynchrony comprises detecting that the plurality of pairs of the brain regions are associated with inter-region correlations above a set of hypersynchrony thresholds; and
detecting a first seizure based on a transition from the period of hyposynchrony to the period of hypersynchrony; wherein detecting the first seizure comprises weighting the transition based on weights assigned to each pair of the plurality of pairs of the brain regions; and
notifying a patient or medical care provider of detection of the first seizure.

19. The method of claim 18, further comprising after the first seizure, modifying the weights based on neural data captured prior to and during the first seizure.

* * * * *